(12) United States Patent
Bille

(10) Patent No.: US 6,641,577 B2
(45) Date of Patent: Nov. 4, 2003

(54) APPARATUS AND METHOD FOR CREATING A CORNEAL FLAP

(75) Inventor: Josef Bille, Heidelberg (DE)

(73) Assignee: 20/10 Perfect Vision Optische Geraete GmbH, Heidelberg (DE)

(*) Notice: Subject to any disclaimer, the term of this patent is extended or adjusted under 35 U.S.C. 154(b) by 0 days.

(21) Appl. No.: 09/997,167

(22) Filed: Nov. 28, 2001

(65) Prior Publication Data

US 2003/0100893 A1 May 29, 2003

(51) Int. Cl.[7] ............................................. A61F 9/008
(52) U.S. Cl. ............................................. 606/4; 128/898
(58) Field of Search .................. 606/4, 12; 128/898

(56) References Cited

U.S. PATENT DOCUMENTS

| | | |
|---|---|---|
| 4,391,275 A | 7/1983 | Fankhauser et al. |
| 4,669,466 A | 6/1987 | L'Esperance |
| 4,764,930 A | 8/1988 | Bille et al. |
| 4,770,172 A | 9/1988 | L'Esperance, Jr. |
| 4,772,115 A | 9/1988 | Gersten et al. |
| 4,773,414 A | 9/1988 | L'Esperance, Jr. |
| 4,887,592 A | 12/1989 | Loertscher |
| 4,988,348 A | 1/1991 | Bille |
| 4,994,058 A | 2/1991 | Raven |
| 5,049,147 A | 9/1991 | Danon |
| 5,062,702 A | 11/1991 | Bille |
| 5,108,412 A | 4/1992 | Krumeich et al. |
| 5,562,656 A * | 10/1996 | Sumiya ........................ 606/4 |
| 6,050,687 A | 4/2000 | Bille et al. |
| 6,280,436 B1 * | 8/2001 | Freeman et al. .............. 606/4 |
| 6,428,533 B1 * | 8/2002 | Bille ............................. 606/4 |

* cited by examiner

Primary Examiner—Roy D. Gibson
Assistant Examiner—Henry M. Johnson
(74) Attorney, Agent, or Firm—Nydegger & Associates

(57) ABSTRACT

A method for creating a corneal flap for use in a corneal reshaping procedure includes the step of creating a periphery for the flap by subsurface photoablation of the cornea using a laser beam. Specifically, tissue located at the interface between layers of stromal lamellae is photoablated to create the periphery. To accomplish this, the size of the bubbles created during photoablation are monitored using a wavefront detector and the photoablation depth is altered when the bubble size indicates that photoablation is not occurring at an interface. With the periphery established, an incision is made into the cornea extending between the anterior surface of the cornea and the periphery. Next, the corneal tissue bounded by the incision is lifted to mechanically separate the flap from the remainder of the cornea along the interface between layers of lamellae.

19 Claims, 3 Drawing Sheets

APPARATUS AND METHOD FOR CREATING A CORNEAL FLAP

FIELD OF THE INVENTION

The present invention pertains generally to ophthalmic laser surgery procedures. More particularly, the present invention pertains to methods for creating corneal flaps for use in corneal reshaping procedures. The present invention is particularly, but not exclusively, useful as a method for using a pulsed laser beam to efficiently create a corneal flap that can be lifted to expose stromal tissue for photoablation.

BACKGROUND OF THE INVENTION

The cornea provides approximately two thirds of the total focusing power of the eye. Along with the lens, the cornea refracts incoming light and focuses the light on or near the retina. The curvature of the cornea determines where the incoming light will be focused. If the curvature of the cornea is too steep relative to the length of the eye, light from distant sources will be focused in front of the retina, causing a vision impairment known as myopia (near-sightedness). Similarly, if the curvature of the cornea is too flat relative to the length of the eye, light from close sources will be focused behind the retina, causing a vision impairment known as hyperopia (far-sightedness). Finally, when the curvature of the cornea is non-uniform, light from both close and distant sources will fail to properly focus on the retina, resulting in a blurring of vision known as astigmatism.

The refractive errors mentioned above can generally be corrected using eyeglasses or contact lenses. Alternatively, the cornea of the eye can be surgically reshaped to provide the needed optical correction. Currently, the most popular technique for reshaping the cornea is laser-assisted in situ keratomileusis (LASIK). In the widely used LASIK procedure, a microkeratome is used to cut a flap in the cornea. Next, the flap is lifted to expose a bed of stromal tissue. Once exposed, the bed of stromal tissue is vaporized to a prescribed depth using an excimer laser. After laser treatment, the flap is repositioned and allowed to heal. The result is a reshaped cornea. Unfortunately, the creation of a flap using a microkeratome can result in some complications. For example, the effective creation of the flap with the microkeratome often relies on the skill of the surgeon. Complications can result if the flap is cut improperly or completely severed from the cornea. Further, use of the microkeratome requires the eye to be restrained from movement, often causing patient discomfort. Additional drawbacks associated with using a microkeratome to create a flap include the inability to control the shape of the flap and the fact that a relatively large amount of corneal tissue needs to be cut to create the flap.

As an example of another corneal reshaping procedure, U.S. Pat. No. 4,907,586, which issued to Bille et al. for an invention entitled "Method for Reshaping the Eye," discloses an intrastromal photoablation technique for reshaping the cornea. Importantly for the purposes of the present invention, the above cited Bille patent discloses the use of a pulsed laser beam for photoablation of intrastromal tissue. Unlike the excimer laser, the pulsed laser beam, as disclosed by Bille, penetrates corneal tissue and can be focused at a point below the surface of the cornea to photoablate stromal tissue at the focal point. The ability to reach a subsurface location without necessarily providing a physical pathway allows for volumes of stromal tissue having complex shapes to be accurately disrupted, while minimizing the amount of total tissue disrupted. The present invention uses subsurface photoablation to create a portion of a corneal flap.

When considering the use of subsurface photoablation to create a flap for corneal reshaping, a general knowledge of the anatomy of the cornea of an eye is helpful. In detail, the cornea comprises various layers of tissue which are structurally distinct. In order, going in a posterior direction from outside the eye toward the inside of the eye, the various layers in a cornea are: an epithelial layer, Bowman's membrane, the stroma, Decemet's membrane, and an endothelial layer. Of these various structures, the stroma is the most extensive and is generally around four hundred microns thick. Additionally, the healing response of the stromal tissue is generally quicker than the other corneal layers. For these reasons, stromal tissue is generally selected for removal in refractive correction procedures.

In detail, the stroma of the eye is comprised of around two hundred identifiable and distinguishable layers of lamellae. Each of these layers of lamellae in the stroma is generally dome-shaped, like the cornea itself, and they each extend across a circular area having a diameter of approximately nine millimeters. Unlike the layer that a particular lamella is in, each lamella in the layer extends through a shorter distance of only about one tenth of a millimeter (0.1 mm) to one and one half millimeters (1.5 mm). Thus, each layer includes several lamellae. Importantly, each lamella includes many fibrils which, within the lamella, are substantially parallel to each other. The fibrils in one lamella, however, are not generally parallel to the fibrils in other lamellae. This is so between lamellae in the same layer, as well as between lamellae in different layers. Finally, it is to be noted that, in a direction perpendicular to the layer, each individual lamella is only about two microns thick.

Somewhat related to the present invention, a method for finding an interface between layers of lamellae for photoablation using a wavefront analyzer and an ellipsometer was disclosed in co-pending U.S. patent application Ser. No. 09/783,665, filed on Feb. 14, 2001 by Bille and entitled "A Method for Separating Lamellae." As such, the contents of co-pending application Ser. No. 09/783,665 are hereby incorporated herein by reference. In co-pending application Ser. No. 09/783,665, a procedure for creating a corneal flap for a LASIK type procedure was presented. Unlike the present invention, the method disclosed in Bille '665 involved using subsurface photoablation to cut the entire inner surface for the flap. The present invention, in contrast, contemplates using subsurface photoablation along an interface solely for the purpose of establishing a periphery for the flap. This periphery, in turn, can be used as a starting point to allow layers of lamellae to be separated from each other along an interface by simply peeling the flap away from the remainder of the cornea.

Within the general structure described above, there are at least three important factors concerning the stroma that are of interest insofar as the creation of a corneal flap is concerned. The first of these factors is structural, and it is of interest here because there is a significant anisotropy in the stroma. Specifically, the strength of tissue within a lamella is approximately fifty times the strength that is provided by the adhesive tissue that holds the layers of lamella together. Thus, much less energy is required to separate one layer of lamella from another layer (i.e. peel them apart), than would be required to cut through a lamella. The second factor is somewhat related to the first, and involves the stromal tissue response to photoablation. Specifically, for a given energy level in a photoablative laser beam, the bubble that is created by photoablation in the stronger lamella tissue will be noticeably smaller than a bubble created between layers of lamellae. The third factor is optical, and it is of interest here because there is a change in the refractive index of the stroma between successive layers of lamellae. This is due to differences in the orientations of fibrils in the respective lamella. When consideration is given to using a laser beam for the purpose of creating a corneal flap in a LASIK procedure, these factors can be significant.

In light of the above, it is an object of the present invention to provide an efficient surgical method for creating a corneal flap suitable for use in a corneal reshaping procedure. Another object of the present invention is to provide a method for creating a corneal flap that minimizes the amount of corneal tissue that must be cut to create the flap. It is yet another object of the present invention to provide a surgical method for creating a corneal flap that allows for the accurate positioning of the corneal flap at a predetermined location on the cornea. It is still another object of the present invention to provide a surgical method for creating a corneal flap that allows for the size and shape of the corneal flap to be closely controlled. Still another object of the present invention is to provide a method for creating a corneal flap that is easy to perform and is comparatively cost effective.

SUMMARY OF THE PREFERRED EMBODIMENTS

In accordance with the present invention, a method for creating a corneal flap suitable for use in a corneal reshaping procedure includes the step of focusing a laser beam to a location between layers of stromal lamellae and photoablating tissue at the interface between these layers. Next, while maintaining the focal point at locations between layers of stromal lamellae, the focal point is moved along a path within the stroma to photoablate a periphery for the flap. With the periphery of the flap established, the edge of the flap is created by making an incision into the cornea that extends from the anterior surface of the cornea to the periphery of the flap.

Once the edge of the flap is created, corneal tissue bounded by the incision can be lifted to mechanically separate the flap from the underlying tissue of the cornea. Specifically, as the corneal tissue bounded by the incision is peeled from the remainder of the cornea, layers of lamellae are mechanically separated from each other to create the flap. More specifically, the layers of lamellae are mechanically separated from each other along the interface between the layers. With the flap created and lifted, an excimer laser can then be used to photoablate exposed stromal tissue and reshape the cornea. After photoablation of the exposed stromal tissue, the flap can be repositioned over the exposed stromal tissue and allowed to heal. The result is a reshaped cornea.

As indicated above, to create the periphery of the flap in accordance with the present invention, the rays of a laser beam must be focused to a location between layers of lamellae to photoablate tissue at the interface between these layers. To position the focal point on the interface between layers, the laser beam is first focused to a start point in the stroma. Preferably, this start point will be at a predetermined distance into the stroma from the anterior surface of the cornea. This predetermined distance will correspond roughly to the desired thickness for the flap (for example, a distance of approximately one hundred and eighty microns can be used).

With the laser beam focused at the start point, tissue at the start point is photoablated by the laser beam to generate a photoablative response (i.e. a bubble is created). The size of this bubble is then measured and compared with a reference value to determine whether the bubble was created on an interface between layers of lamellae or inside a lamella. The measurement of the bubble is preferably accomplished with a wavefront detector. If it is determined that the initial bubble was created inside a lamella, a subsequent bubble is created at a different point in the stroma. In most cases, this subsequent bubble is created at a shorter depth from the anterior surface of the cornea than the initial bubble. The new bubble is then compared to the reference value to determine whether the new bubble was created on an interface between layers of lamellae. This process is continued until a bubble is created having a bubble size indicating that photoablation is occurring on an interface between layers of lamellae.

For the purposes of the present invention, the reference value is chosen to correspond to a hypothetical gas bubble in the stroma that, as a result of photoablation, would have a diameter of approximately fifteen microns. A condition wherein the measured bubble is greater than the reference value is indicative that the photoablation of issue is occurring in the weaker tissue that is located on an interface between layers of lamellae rather than inside of a lamella.

Once a bubble is created indicating that photoablation has occurred at a location on an interface between layers of stromal lamellae, the focal point of the laser is moved along a path within the stroma to photoablate the periphery of the flap. As the laser is moved along the path, the focal point is maintained on the interface between layers of stromal lamellae. From the first point found on the interface, the next point selected for photoablation along the path is chosen at approximately the same depth as the first point. After the photoablation of each point, the resulting bubble is measured and compared to the reference to ensure that photoablation is occurring on the interface. In this manner, photoablation along the path is continued at a constant depth until the measured bubble is less than the reference value. When a bubble is measured to be less than the reference value, the indication is that the focal point is no longer positioned on the interface. When the focal point is no longer positioned on the interface, the depth of the focal point is altered until a bubble is produced that is larger than the reference value (indicating that photoablation is again occurring on the interface).

The process described above is continued until the periphery of the flap is completed. The resulting periphery consists of a cut along an interface between layers of stromal lamellae. Generally, the periphery follows a curved line that is centered approximately on the optical axis of the eye and extends through an arc of about two hundred and seventy degrees. Typically, the entire periphery can be created on a single common interface between layers of lamellae. For this purpose, an ellipsometer is provided to detect a birefringent condition at each location that is photoablated. Specifically, this birefringent condition results from the orientation of fibrils in the lamella. Further, it is known that from one interface between layers of lamellae to another there will be a birefringent change that is manifested as a change in phase of about one half degree. In accordance with the present invention, the detection of the birefringent change can indicate a change from one interface to another. Consequently, detection of the birefringent change can be used to establish and maintain the focal point on a single interface between layers of lamellae while the focal point is moved along the path to cut the periphery for the flap. The result is a periphery for the flap that is created on a single interface between layers of lamellae.

In some cases, due to the anatomy of the cornea or the shape of the desired flap, the entire periphery cannot be created on a single interface between layers of lamellae. In these cases, two or more interfaces may need to be photoablated to create the periphery of the flap. When this is required, it may be advantageous to alter the energy level of the laser beam when transitioning from one interface to another. Specifically, a higher energy is generally required to efficiently photoablate within a layer of lamellae than is required to efficiently photoablate on an interface between layers of lamellae. For example, an energy of approximately five microjoules for a ten micron diameter spot size is suitable for photoablation on an interface between layers of lamellae, while a somewhat larger energy is more efficient for photoablation within a layer of lamellae.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
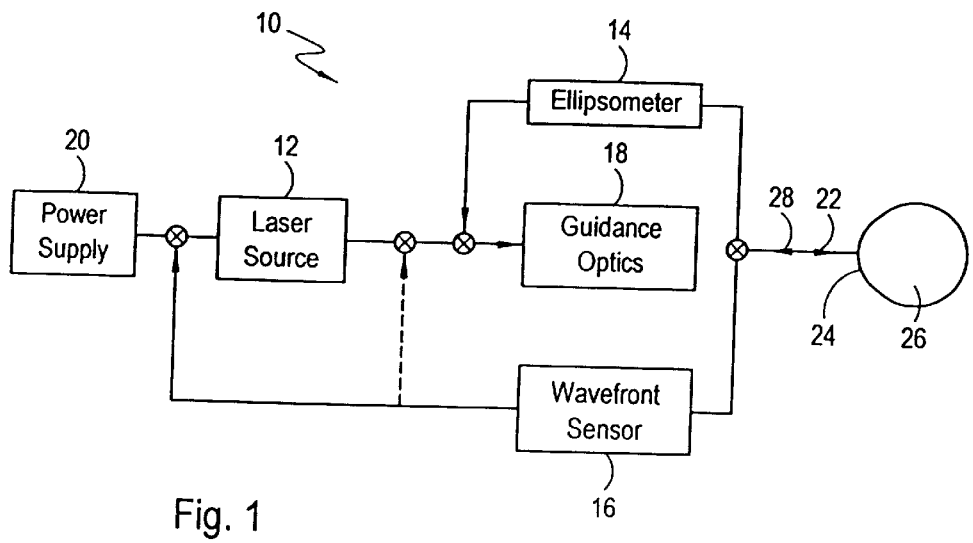
FIG. 1 is a schematic diagram, in a closed-loop feedback control format, showing the operative components of an apparatus that is useful for performing the methods of the present invention.

Referring initially to FIG. 1, an apparatus for use in performing the methods of the present invention is shown schematically in a control loop format and is generally designated 10. As shown, the apparatus 10 includes a laser source 12 which, preferably, is capable of generating a continuous train of ultra-short pulses, with each pulse having a pulse duration of approximately one pico-second. Specifically, it is necessary that each pulse have an energy level that is above the threshold necessary for the photoablation of stromal tissue (i.e. above approximately one and one half microjoules per ten micron diameter spot size). The apparatus 10 also includes an ellipsometer 14 that is capable of determining the birefringent properties within stromal tissue. For the purposes of the present invention, an ellipsometer of the type disclosed and claimed in U.S. Pat. No. 5,822,035, which issued to Bille for an invention entitled "Ellipsometer," is suitable. Furthermore, FIG. 1 shows that the apparatus 10 includes a wavefront detector 16, such as a Hartmann-Shack sensor, which is capable of modeling a wavefront. Additionally, the apparatus 10 includes guidance optics 18 that are capable of steering and focusing a laser beam onto predetermined focal points. A power unit 20 is also provided. In combination, these components cooperate with each other to generate a laser beam 22 that is directed to a focal point in the cornea 24 of an eye 26 with a predetermined energy level. Control over this operation, to include the location of the focal point and its energy level, is made possible by using the ellipsometer 14 and the wavefront detector 16 to monitor reflected light 28 as it is reflected from the cornea 24.

Figure 2:
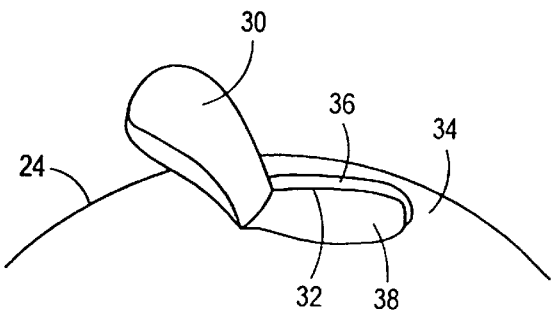
FIG. 2 is a perspective view of a corneal flap.
Figure 3:
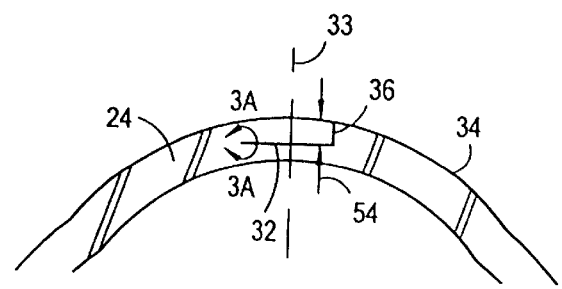
FIG. 3 is a sectional view of a cornea after the periphery and edge of a flap have been established.
Figure 4:
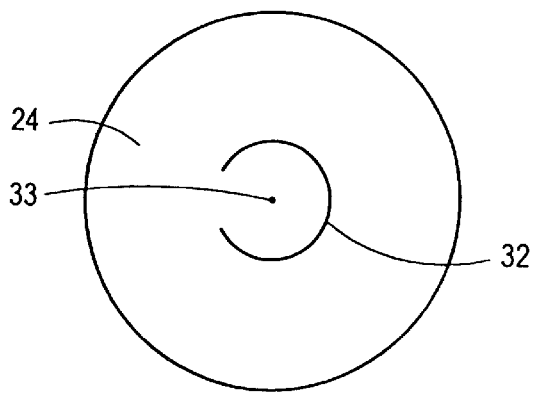
FIG. 4 is a plan view of a cornea after the periphery and edge of a flap have been established.

Referring now to FIGS. 2–4, a corneal flap 30 prepared in accordance with the present invention is shown. As detailed further below, the flap 30 is prepared by first cutting a periphery 32 for the flap 30. As best seen with cross-reference to FIGS. 2 and 3, a typical periphery 32 follows a curved line that is centered approximately on the optical axis 33 of the eye 26 and extends through an arc of about two hundred and seventy degrees. With the periphery 32 established, an incision can be made extending from the anterior surface 34 of the cornea 24 to the periphery 32 to establish an edge 36 for the flap 30. Once the edge 36 is created, the flap 30 can be peeled from the remainder of the cornea 24 to expose a bed of stromal tissue 38. After exposure, the bed of stromal tissue 38 can be photoablated using an excimer laser (not shown). After photoablation with the excimer laser, the flap 30 can be repositioned over the bed of stromal tissue 38 and allowed to heal. The result is a reshaped cornea 24.

Figure 3A:
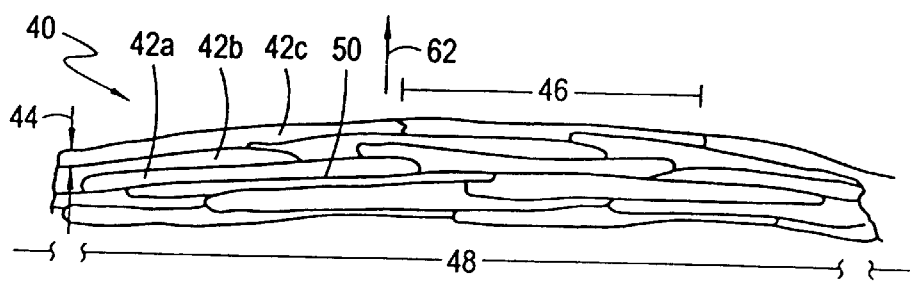
FIG. 3A is an enlarged sectional view of the cornea as seen by enclosing line 3—3 in FIG. 3, showing an interface between layers of stromal lamellae.

In FIG. 3A, a portion of the stroma 40 in the cornea 24 is shown to include a plurality of lamellae 42, of which the lamellae 42a, 42b and 42c are only exemplary. Dimensionally, each of the lamellae 42 in the stroma 40 have a depth 44 that is approximately two microns, and a width 46 that is between approximately one tenth and one and one half millimeters. Thus, the lamellae 42 each have a very thin disk shape. Anatomically, the lamella 42 lie on top of each other in layers that extend across the cornea 24 through a distance 48 that is approximately nine millimeters. As shown in FIG. 3A, the individual lamella 42 overlap to some extent and are somewhat randomly arranged in layers. Also shown, adjacent layers of lamellae 42 are separated by interfaces 50 of which the interface 50 shown in FIG. 3A is exemplary. In general, the interfaces 50 are substantially parallel to each other and extend all the way across the cornea 24. Importantly, tissue at the interface 50 has different characteristics and behaves differently during photoablation than the tissue inside a lamella 42.

With cross reference now to FIGS. 3 and 3A, it is to be appreciated that in accordance with the present invention, the periphery 32 for the flap 30 is created by photoablating a path along an interface 50 between layers of lamellae 42. With the periphery 32 established at an interface 50, an incision extending from the anterior surface 34 of the cornea 24 to the periphery 32 can be made with a surgical knife to establish the edge 36 for the flap 30. If desired, the incision from the anterior surface 34 of the cornea 24 to the periphery 32 can be made with a pulsed laser beam 22 (shown in FIG. 1) or any other technique known in the pertinent art. Importantly, since the periphery 32 is established at an interface 50, corneal tissue bounded by the edge 36 can be lifted to peel one layer of lamella 42 from another layer of lamella 42 along the interface 50 to establish the flap 30.

Figure 5:
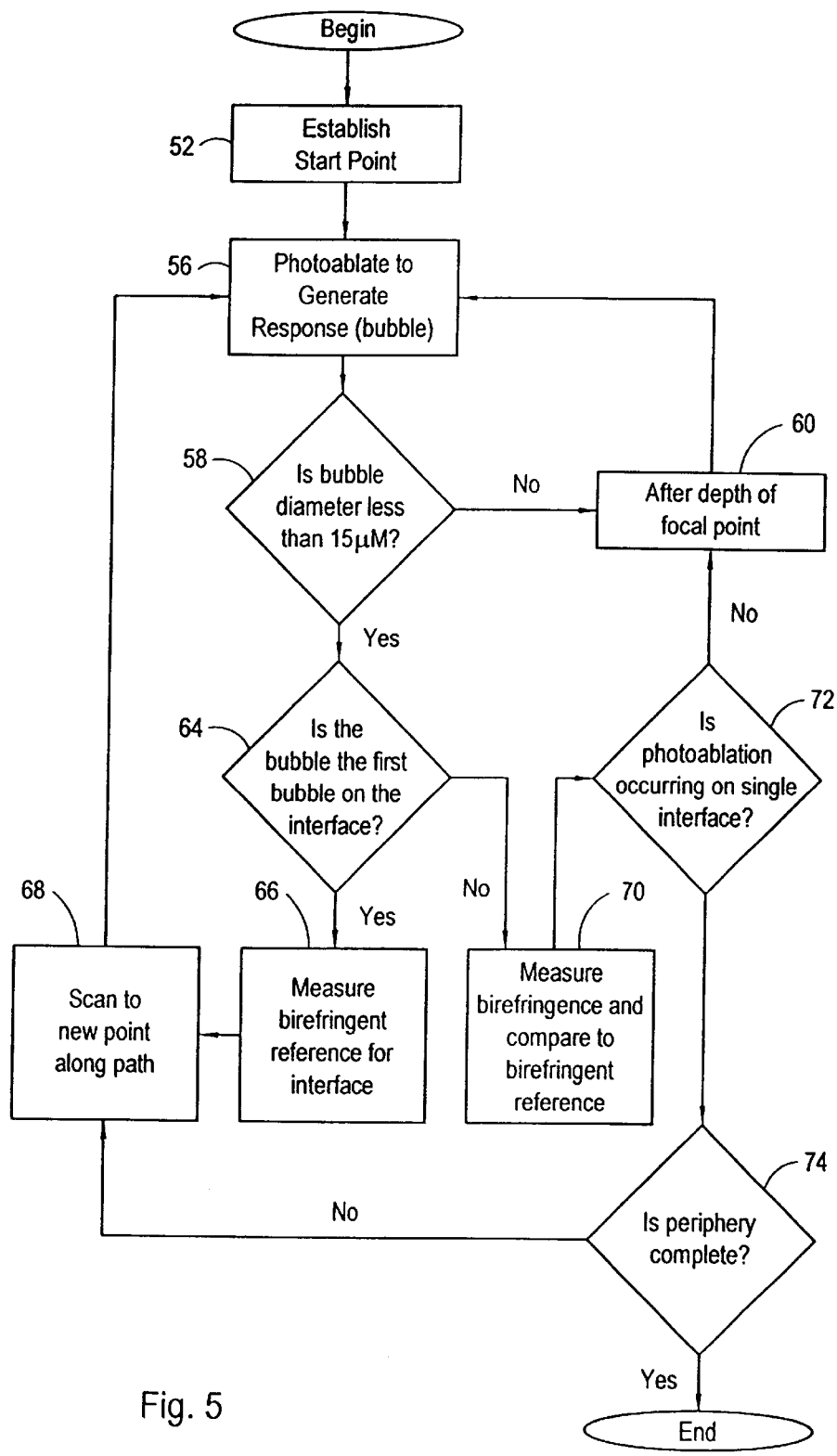
FIG. 5 is a logic flow chart of the sequential steps to be accomplished in accordance with the methods of the present invention.
Figure 5:
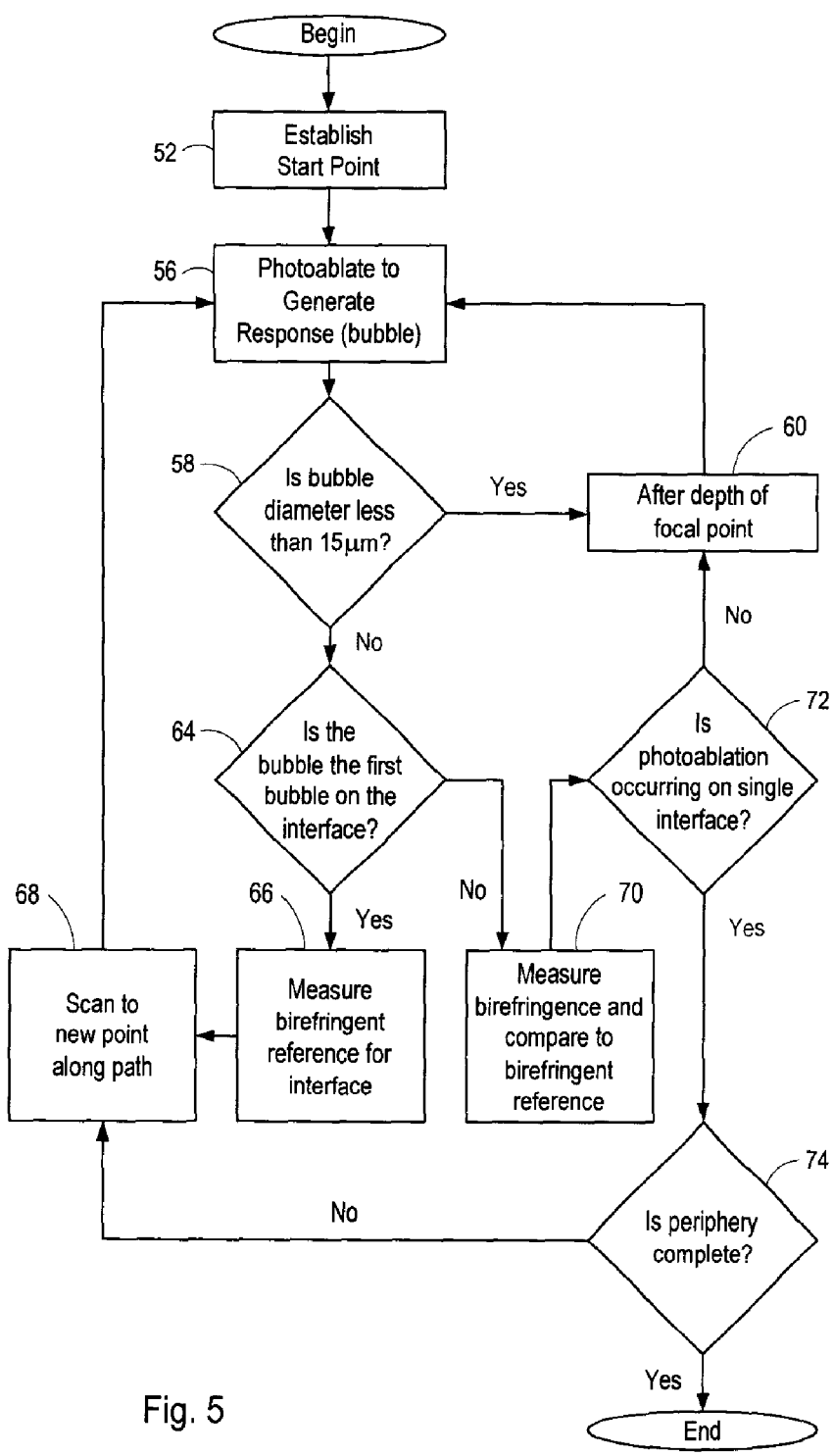

With cross reference now to FIGS. 3, 3A and 5, the operation of apparatus 10 to create a periphery 32 on an interface 50 between layers of lamellae begins by establishing a start point (action block 52) in the stroma 34 of cornea 24. Specifically, the start point is established at a distance 54 that is measured from the anterior surface 34 of the cornea 24 in a direction that is substantially perpendicular to the anterior surface 34. As intended for the apparatus 10, the exact location of the anterior surface 34 can be determined using the wavefront detector 16, and the distance 54 which will define the thickness of the flap 30 can then be arbitrarily chosen to be around about one hundred and eighty microns from the anterior surface 34.

Once a start point has been established in the stroma 40, action block 56 in FIG. 5 indicates that the next step in the methods of the present invention is to photoablate tissue at the start point to create a response (i.e. a bubble in the stromal tissue). As indicated by inquiry block 58, this response is then compared with a reference (e.g. 15 μm). For a given energy level, the size of the bubble that is formed will be a function of the type of tissue photoablated. In this case, with the same energy level, the stronger tissue inside a lamella 42 will yield a smaller bubble and the weaker tissue at an interface 50 will yield a larger bubble. Fortunately, as used for the present invention, the respective sizes of the bubbles will serve as photoablative responses that can be measured by the wavefront detector 16 using relatively well known wavefront techniques. Accordingly, the photoablative response of a bubble can be compared with a reference value to determine whether the bubble resulted from photoablation on an interface 50 or inside a lamella 42.

Continuing with FIG. 3A, if the response is smaller than the reference, action block 60 indicates that the depth of the focal point should be altered (i.e. the distance 54 should be changed). This change in distance 54 will preferably be taken in an anterior direction (indicated by the arrow 62 in FIG. 3A) and will, most likely, be less than approximately two microns. After altering the depth of the focal point, FIG. 5 shows that the new point is photoablated (action block 56) and the new bubble is measured and compared to the reference (inquiry block 58). This process (blocks 56, 58 and 60) is continued until a bubble results that is greater than the reference (e.g. 15 μm), indicating that photoablation is occurring on an interface 50.

Once a first bubble has been found on an interface 50 (inquiry block 64), the reflected light 28 from cornea 24 can be monitored by the ellipsometer 14 to determine a birefringent reference (action block 66) for the interface 50. As discussed above, a different birefringence will be measured from one interface 50 to another. This change in birefringent properties is due to changes in the orientation of fibrils (not shown) in the lamella 42. Thus, by measuring the birefringent properties for different points within the stroma 40, it can be determined whether the different points are located on a common interface 50. Once the birefringent reference is measured for the interface 50, action block 68 shows that the next step is to scan the focal point of the laser beam 22 (shown in FIG. 1) along the desired path to create the periphery 32.

Upon photoablation at the new location (action block 56), the resultant bubble is compared with the reference standard bubble (inquiry block 58). Thus, a determination is made whether the new location is on an interface 50 or inside a lamella 42. If the response is smaller than the reference, action block 60 indicates that the depth of the focal point should be altered. This process (blocks 56, 58 and 60) is continued until a bubble results that is greater than the reference (e.g. 15 μm), indicating that photoablation is occurring on an interface 50. Next, action block 66 indicates that the next step is to measure the birefringent properties at the new location (action block 70) using an ellipsometer 14, for comparison to the birefringent reference. As indicated by inquiry block 72, this measurement (i.e. action block 70) can be used to determine whether the new location is on the same interface 50 as the previous photoablation point. It will happen that locations on two different interfaces 50 will result in a birefringent change on the order of plus or minus one half degree.

Referring still to FIG. 5, inquiry block 72 indicates that when the new bubble is not located on the proper interface 50, the depth of the focal point is altered (action block 60). Next, blocks 56, 58, 70 and 72 are repeated until a point is located that is on the proper interface 50. When a point is located that is on the proper interface 50, and inquiry block 74 indicates that the periphery 32 is not complete, then the process is continued (starting at action block 68) until the periphery is completed.

When the entire periphery 32 cannot be created on a single interface 50 between layers of lamellae 42 due to the anatomy of the cornea 24 or the shape of the desired flap 30, two or more interfaces 50 may need to be photoablated to create the periphery 32 of the flap 30. When this is required, it may be advantageous to alter the energy level of the laser beam 22 (shown in FIG. 1) when cutting from one interface 50 to another. Specifically, a higher energy is generally required to efficiently photoablate within a layer of lamellae 42 than is required to efficiently photoablate on an interface 50. For example, an energy of approximately five microjoules for a ten micron diameter spot size is suitable for photoablation on an interface 50, while a somewhat larger energy is more efficient for photoablation within a layer of lamellae 42.

Figure 6:
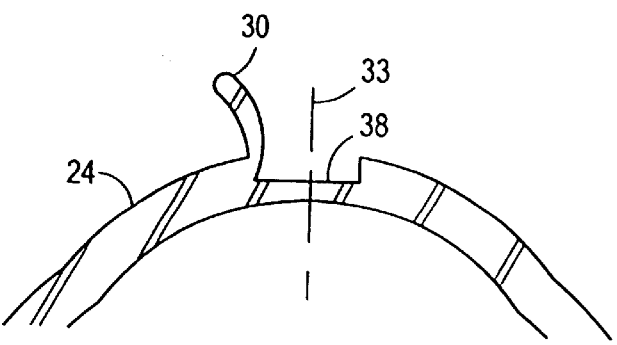
FIG. 6 is a sectional view of a corneal flap, after the flap has been peeled back from the remainder of the cornea.

With reference now to FIGS. 3 and 6, it can be seen that after the periphery 32 is established, an incision extending between the anterior surface 34 of the cornea 24 and the periphery 32 can be made with either a surgical laser or with a surgical knife, as desired by the operator, to establish the edge 36 for the flap 30. Importantly, since the periphery 32 is established at an interface 50, corneal tissue bounded by the edge 36 can be lifted to peel one layer of lamella 42 from another layer of lamella 42 along the interface 50 to establish the flap 30.

While the particular Method for Creating a Corneal Flap as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for creating a corneal flap for an ophthalmic procedure, said method comprising the steps of:

directing a laser beam to a focal point at a location on an interface between layers of stromal lamellae to photoablate stromal tissue at said focal point;

moving said focal point along a predetermined path within the stroma to another location to repeat said directing step to photoablate a periphery for said flap;

incising the cornea between the anterior surface of the cornea and said periphery to crate an edge for said flap; and separating layers of stromal lamellae from each other at said interface to create said flap, with said flap being bounded by said edge.

2. A method as recited in claim 1 wherein said directing step comprises the steps of:

focusing the rays of a laser beam to star point in the stroma to photoablate stromal tissue at said start point and create a gas bubble in response thereto, said gas bubble having a diameter;

comparing said diameter of said gas bubble to a reference value to determine whether said bubble is in an interface between layers of stromal lamellae;

repositioning said laser beam to focus the rays of said laser beam at another point when said comparing step indicates that said bubble is not on an interface between layers of stromal lamellae; and repeating said comparing and repositioning steps until a bubble results that is on an interface between layers of stromal lamellae.

3. A method as recited in claim 2 wherein said comparing step is accomplished by employing a wavefront detector.

4. A method as recited in claim 2 wherein said reference value is indicative of a gas bubble in the stroma having a diameter of approximately fifteen microns.

5. A method as recited in claim 1 wherein said incising step is accomplished with a laser beam.

6. A method as recited in claim 1 wherein said incising step is accomplished with a blade.

7. A method as recited in claim 1 wherein said separating step is accomplished by mechanically peeling said layers of stromal lamellae from each other at said interface.

8. A method as recited in claim 1 wherein said periphery is a curved line having a radius of curvature of approximately four and one half millimeters and said curved line extends through an arc of approximately two hundred and seventy degrees.

9. A method for creating a corneal flap for an ophthalmic procedure, said method comprising the steps of:

photoablating stromal tissue at a focal point at a predetermined depth from the anterior surface of the cornea to create a gas bubble in response thereto, said gas bubble having a diameter;

comparing said diameter of said gas bubble to a reference value to determine whether said bubble is on an interface between layers of stromal lamellae;

altering the depth of said focal point when said comparing step indicates that said bubble is not on an interface between layers of stromal lamellae;

repeating said photoablating, comparing and altering steps until a bubble results that is on an interface between layers of stromal lamellae;

moving said focal point along a predetermined path within the stroma to successive locations to perform said photoablating, comparing, altering and repeating steps at each said successive location to photoablate a periphery for said flap;

incising the cornea between the anterior surface of the cornea and said periphery to create an edge for said flap; and separating layers of stromal lamellae from each other at said interface to create said flap, with said flap being bounded by said edge.

10. A method as recited in claim 9 wherein said comparing step is accomplished by employing a wavefront detector.

11. A method as recited in claim 9 wherein said reference value is indicative of a gas bubble in the stroma having a diameter of approximately fifteen microns.

12. A method as recited in claim 9 wherein said incising step is accomplished with a pulsed laser beam.

13. A method as recited in claim 9 wherein said incising step is accomplished with a surgical knife.

14. A method as recited in claim 9 wherein said separating step is accomplished by mechanical peeling said layers of stromal lamellae from each other at said interface.

15. A method as recited in claim 9 further comprising the steps of:

using and ellipsometer to measure a birefringent property for a first bubble and a second bubble that are on an interface between layers of stromal lamellae; and varying the depth of said local point before photoablating at a successive location when the birefringent property measurement of said second bubble is not approximately equal to the birefringent property measurement of said first bubble.

16. A method as recited in claim 9 wherein said periphery is a curved line having a radius of curvature of approximately four and one half millimeters and said curved line extends through an arc of approximately two hundred and seventy degrees.

17. An apparatus for creating a corneal flap for an ophthalmic procedure, said apparatus comprising:

a laser source for creating a laser beam;

a means for directing said laser to a focal point at a location on an interface between layers of stromal lamellae to photoablate stromal tissue at said focal point;

a means for moving said focal point along a predetermined path within the stroma to photoablate a periphery for said flap; and a means for incising the cornea between the anterior surface of the cornea and said periphery to create an edge for said flap allowing;

said layers of stromal lamellae to be separated from each other at said interface to create said flap, with said flap being bounded by said edge.

18. An apparatus as recited in claim 17 wherein said directing means comprises a wavefront detector to measure bubbles created during photoablation to determine whether photoablation is occurring on an interface between layers of stromal lamellae.

19. An apparatus as recited in claim 17 wherein said laser source is a pulsed laser source.

* * * * *

UNITED STATES PATENT AND TRADEMARK OFFICE
CERTIFICATE OF CORRECTION

PATENT NO. : 6,641,577 B2
DATED : November 4, 2003
INVENTOR(S) : Josef Bille

It is certified that error appears in the above-identified patent and that said Letters Patent is hereby corrected as shown below:

Column 4,
Line 21, delete "issue" insert -- tissue --

Column 9,
Line 4, delete "in" insert -- on --

Column 10,
Line 13, delete "mechanical" insert -- mechanically --
Line 20, delete "local" insert -- focal --

Signed and Sealed this

Ninth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,641,577 B2  
DATED : November 4, 2003  
INVENTOR(S) : Josef Bille Page 1 of 2

It is certified that error appears in the above-identified patent and that said Letters Patent is hereby corrected as shown below:

Drawings,
Please replace old fig 5 with attached Figure 5

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,641,577 B2 Page 1 of 1
APPLICATION NO. : 09/997167
DATED : November 4, 2003
INVENTOR(S) : Josef Bille It is certified that error appears in the above-identified patent and that said Letters Patent is hereby corrected as shown below:

Column 8, Line 59
DELETE
" crate "
INSERT
-- create --

Signed and Sealed this

Eighteenth Day of September, 2007

JON W. DUDAS
*Director of the United States Patent and Trademark Office*